United States Patent
Robertson et al.

(10) Patent No.: US 9,336,795 B1
(45) Date of Patent: May 10, 2016

(54) SPEECH THERAPY SYSTEM AND METHOD WITH LOUDNESS ALERTS

(71) Applicants: Mark Andrew Robertson, Murrieta, CA (US); Clifford Jay Griffin, Murrieta, CA (US); Karen Lynn Griffin, Murrieta, CA (US)

(72) Inventors: Mark Andrew Robertson, Murrieta, CA (US); Clifford Jay Griffin, Murrieta, CA (US); Karen Lynn Griffin, Murrieta, CA (US)

(73) Assignee: Griffin Laboratories, Temecula, CA (US)

(*) Notice: Subject to any disclaimer, the term of this patent is extended or adjusted under 35 U.S.C. 154(b) by 0 days.

(21) Appl. No.: 14/658,069

(22) Filed: Mar. 13, 2015

Related U.S. Application Data (60) Provisional application No. 62/008,535, filed on Jun. 6, 2014.

(51) Int. Cl.
*G10L 25/48* (2013.01)
(52) U.S. Cl.
CPC .................................. *G10L 25/48* (2013.01)
(58) Field of Classification Search
CPC ....................................................... G10L 25/48
USPC ................................................. 704/200–274
See application file for complete search history.

(56) References Cited

U.S. PATENT DOCUMENTS

| | | | | |
|---|---|---|---|---|
| 8,370,163 B2* | 2/2013 | Faisman | ................. | G10L 15/24 704/231 |
| 8,756,065 B2* | 6/2014 | Melamed | ............ | G06F 17/2715 704/231 |
| 2009/0264789 A1* | 10/2009 | Molnar | .............. | A61N 1/36135 600/544 |

* cited by examiner

*Primary Examiner* — Marcellus Augustin
(74) *Attorney, Agent, or Firm* — Loyal McKinley Hanson (57) ABSTRACT

A speech therapy system includes a portable voice-monitoring assembly with a voice-sensing first subassembly and a loudness-alert-producing second subassembly. The second subassembly (e.g., a microcontroller-outfitted electronic circuit) produces loudness alerts using a selected one of multiple loudness alert types to better aid the user keep speech characteristics (e.g., speech volume) within a specified range of acceptable voicing. Preferably, the second subassembly records a USAGE TIME parameter, and changes the loudness alert type if the USAGE TIME parameter exceeds a specified value. Preferably, the second subassembly records an EFFECTIVENESS parameter, based upon the duration of use required before the user adjusts their speech to acceptable voicing, and changes the loudness alert type if the EFFECTIVENESS parameter falls below a specified value. Preferably, alerts are included to indicated when voicing levels exceed user-inputted maximum and minimum levels. The methodology of the present invention proceeds accordingly.

6 Claims, 13 Drawing Sheets

Fig. 13

SPEECH THERAPY SYSTEM AND METHOD WITH LOUDNESS ALERTS

CROSS REFERENCE TO RELATED APPLICATION

This application claims the benefit under 35 USC 119(e) of U.S. Provisional Patent Application Ser. No. 62/008,535 filed Jun. 6, 2014.

BACKGROUND OF THE INVENTION

1. Technical Field

This invention relates generally to speech therapy, and more particularly to a speech therapy system that provides real-time loudness alerts to a patient experiencing hyperphonia or hypophonia.

2. Description of Related Art

The term "loudness alerts" herein includes audible sounds provided to a patient as a realtime alert that the patient is speaking too softly (i.e., hypophonia) or too loudly (i.e., hyperphonia). Such loudness alerts may take any of various forms, including a "beep," a brief period of white noise, a constant tone, or even the playing of an audio ".wav" file. An electronic module (i.e., a phonation monitor) that the patient wears or otherwise carries in the treatment of Parkinson's disease or phonotrauma autism (or other speech-affecting condition), produces the loudness alerts via an accompanying headset, earpiece, or other audio-producing transducer worn by the patient. The patient responds to the loudness alerts by adjusting their speech toward a desired voice level.

The voice-monitoring module available under the trademark "VOCALOG" from Griffin Laboratories of Temecula, Calif., provides an example. It includes electronic circuitry that collects speech data from the patient for up to three weeks to assist the clinician in identifying vocal patterns. In one form, the voice-monitoring module is mounted directly on the neckband of a Griffin Laboratories throat microphone along with an earpiece. That arrangement results in an effective speech therapy system referred to as a "vocal activity monitor." The patient wears the vocal activity monitor on their neck in order to receive discreet loudness alerts via the module-and-earpiece combination for constant, on-the-go, realtime, biofeedback.

In operation, the throat microphone of the vocal activity monitor produces an electrical input signal indicative of the patient's vocal activity. That input signal is coupled to the electronic circuitry of the voice-monitoring module where its characteristics are compared with a table of parameters to determine if a loudness alert should be initiated. If a loudness alert is indicated (e.g., the patient is speaking too softly), the type of loudness alert to be produced is first determined according to stored parameters that the user had inputted to the module earlier. As the desired type of loudness alert is determined, the module produces an electrical loudness alert output signal, while sending the output signal to the audio-feedback component of the vocal activity monitor in order to produce an audible loudness alert sound for the patient's benefit.

Such loudness alerts prove to be quite effective in many respects. Some patients, however, need ongoing variation in the type of loudness alert produced, together with advantageous variation in frequency and volume. In addition, some patients exhibit a tendency to become calloused to the loudness alerts (i.e., insensitive or emotionally hardened). After awhile, they seem to ignore the loudness alerts altogether. For these and other reasons, a need exists for improvements in loudness-alerts equipment and techniques.

SUMMARY OF THE INVENTION

In view of the foregoing, it is a primary object of the present invention to provide a voice-monitoring system that meets the needs and alleviates the concerns outlined above. The present invention achieves this objective by providing a portable voice-monitoring system that produces loudness alerts while varying the loudness alerts according to the user's vocal activity. The system monitors user vocal activity and produces realtime variations in the loudness alerts according to predetermined criteria, based upon cumulative usage time and effectiveness of the loudness alerts produced.

To paraphrase some of the more precise language appearing in the claims and further introduce the nomenclature used, a speech therapy system constructed according to the present invention includes a portable voice-monitoring assembly for a user to carry and use as an aid to maintaining their speech in a specified range of acceptable voicing. A voice-sensing first subassembly of the portable voice-monitoring assembly (e.g., microphone components) produces an electrical signal indicative of speech spoken by the user. An alert-producing second subassembly portion of the portable assembly (e.g., a microcontroller-outfitted electronic circuit) receives the electrical signal and produces a loudness alert to the user when the electrical signal indicates that the speech spoken by the user falls outside the specified range of acceptable voicing.

According to a major aspect of the present invention, the alert-producing second subassembly is configured to produce a plurality of loudness alert types from which a currently used loudness alert type is selected. Preferably, the alert-producing second subassembly includes digital microcontroller circuitry that is configured (i.e., programmed) to record a USAGE TIME parameter for the currently used loudness alert type (i.e., a parameter stored in memory), and to change the currently used loudness alert type (in conjunction with resetting the USAGE TIME parameter) if the USAGE TIME parameter exceeds a specified value. Preferably, the alert-producing second assembly is configured to record an EFFECTIVENESS parameter for the currently used loudness alert type based upon the duration of use before the user adjusts their speech to within the specified range of acceptable voicing, and change the currently used loudness alert type (in conjunction with resetting the EFFECTIVENESS parameter) if the EFFECTIVENESS parameter falls below a specified value. Preferably, loudness alerts are provided to indicate when voicing exceeds maximum and minimum voicing levels.

In line with the above, there is provided a method for producing a loudness alert when the speech of the user falls outside a specified range of acceptable voicing. The method includes a step of providing a voice-monitoring assembly as described above. It proceeds by (I) monitoring the speech of the user with said voice-monitoring assembly, (ii) determining with said voice-monitoring assembly if the speech falls outside the specified range of acceptable voicing, (iii) selecting with the second subassembly one of the plurality of loudness alert types to be used as the currently used loudness alert type, and (iv) producing a loudness alert with the second subassembly using the currently used loudness alert type if the speech falls outside the specified range of acceptable voicing. Preferably, the methodology takes into account loudness-alerts usage time, effectiveness, and maximum and minimum voicing levels, all as described above for the speech therapy system.

Thus, the present invention provides a speech therapy system and method with loudness alerts that significantly aid a user in maintaining their speech within a range of acceptable voicing. The following illustrative drawings and detailed description make the foregoing and other objects, features, and advantages of the invention more apparent.

DESCRIPTION OF THE PREFERRED EMBODIMENTS

Figure 1:
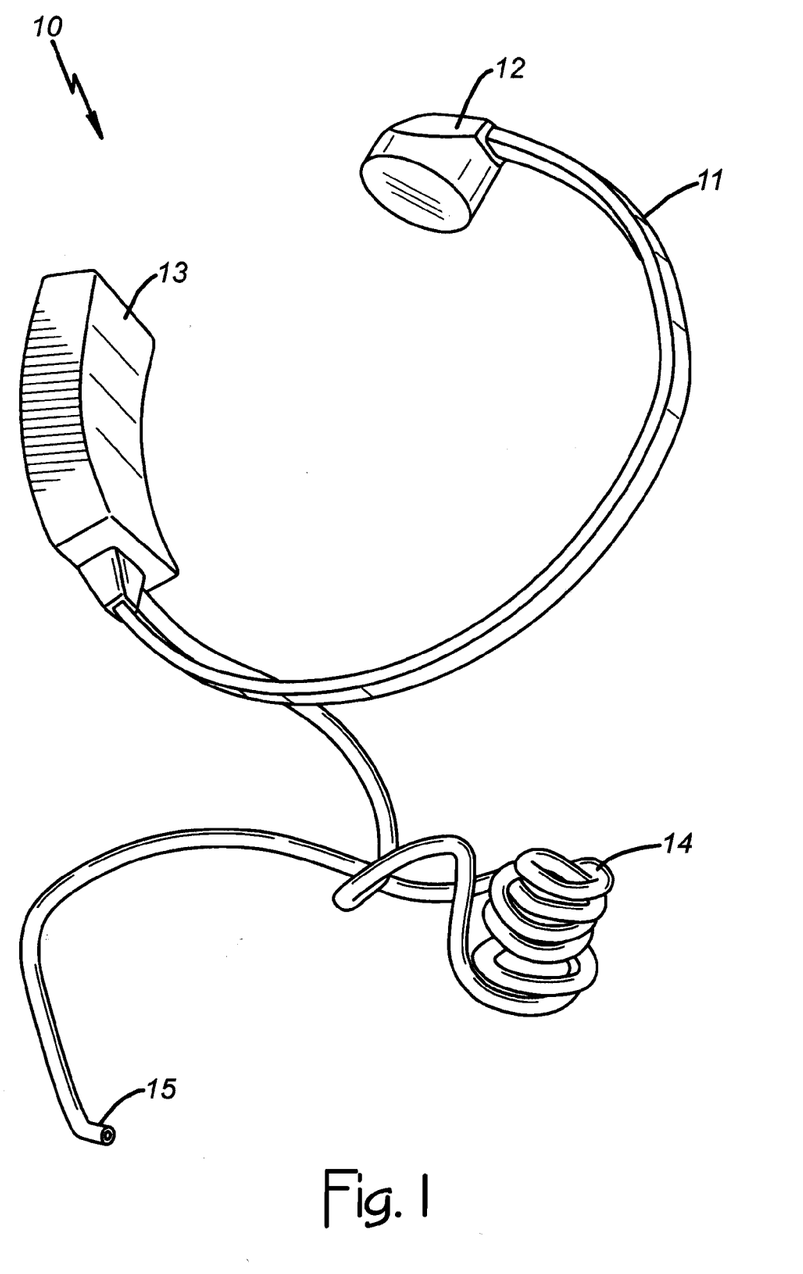
FIG. 1 of the drawings is a perspective view of a throat microphone assembly that includes a voice-monitoring module constructed according to the present invention.

FIG. 1 of the drawings shows a speech therapy system constructed according to the present invention in the form of a throat-microphone assembly 10. The assembly 10 is presented as just one example of an assembly embodying the structure and methodology of the present invention. The throat-microphone assembly 10 functions as a type of phonation monitor or vocal activity monitor that provides real-time loudness alerts to a user (not shown), and it includes a neck band 11 that encircles most of the neck of the user as a support. The neck band 11 supports a sensor component (i.e., a sensor subassembly 12) so that the sensor subassembly 12 is held against the neck of the user; it also supports an electronic module (i.e., a module subassembly 13) in the general vicinity of an ear of the user, and it supports cabling (not shown) that couples an electrical signal from the sensor subassembly 12 to the electronic module 13.

In use, with the assembly 10 worn on the neck of the user, the sensor subassembly 12 produces a time-varying electrical signal indicative of audio information (i.e., information about vibrations of the user's neck resulting from speech produced by the user. The module subassembly 13 (e.g., digital microcontroller circuitry that operates under program control) processes that electrical signal in order to produce audible loudness alerts that a tube 14 (e.g., a flexible plastic tube functioning as an acoustic channel) couples via a distal end 15 of the tube 14 to an ear canal of the user. The user thereby receives discreet loudness alerts in their ear canal from the module subassembly 13 via the tube 14 for constant, on-the-go, realtime, biofeedback.

The sensor subassembly 12 functions as means for sensing vibrations that result from speech produced by the user, while the neck band 11 functions as means for holding the sensor subassembly 12 against the neck of the user, preferably in a frontal placement position of the sensor subassembly 12 such that the sensor component 12 is located front and center of the neck, between the sternal notch and the larynx. The sensor subassembly 12 (e.g., a known type of contact microphone, air-displacement microphone, and/or other transducer component) responds to vibrations produced when the user speaks by creating an electrical signal that is coupled via a cable to the module subassembly 13. The throat microphone assembly 10 holds the sensor subassembly 12 in an advantageous manner enhancing that function.

The illustrated neck band 11 includes a flat metal component that is covered by a plastic sleeve or coating. The flat metal component is, for example, an approximately seven-inch to eight-inch long (for children) and up to about fifteen-inch long for adults (depending on neck size) length of spring steel having a width of about 0.200 inches to 0.250 inches and a thickness of about 0.020 inches, although other kinds and types of flat component (i.e., resiliently deformable and recovering) may be used within the scope of the present invention. The neck band 11 includes a first end portion (i.e., a module-holding end portion), a second end portion (i.e., a sensor-holding end portion), and an intermediary portion (i.e., a neck-encircling portion). The user chooses a particular one of various neck band sizes to fit the circumference of the user's neck so that the neck band 11 holds the sensor subassembly 12 securely in the frontal placement position mentioned above.

Figure 2:
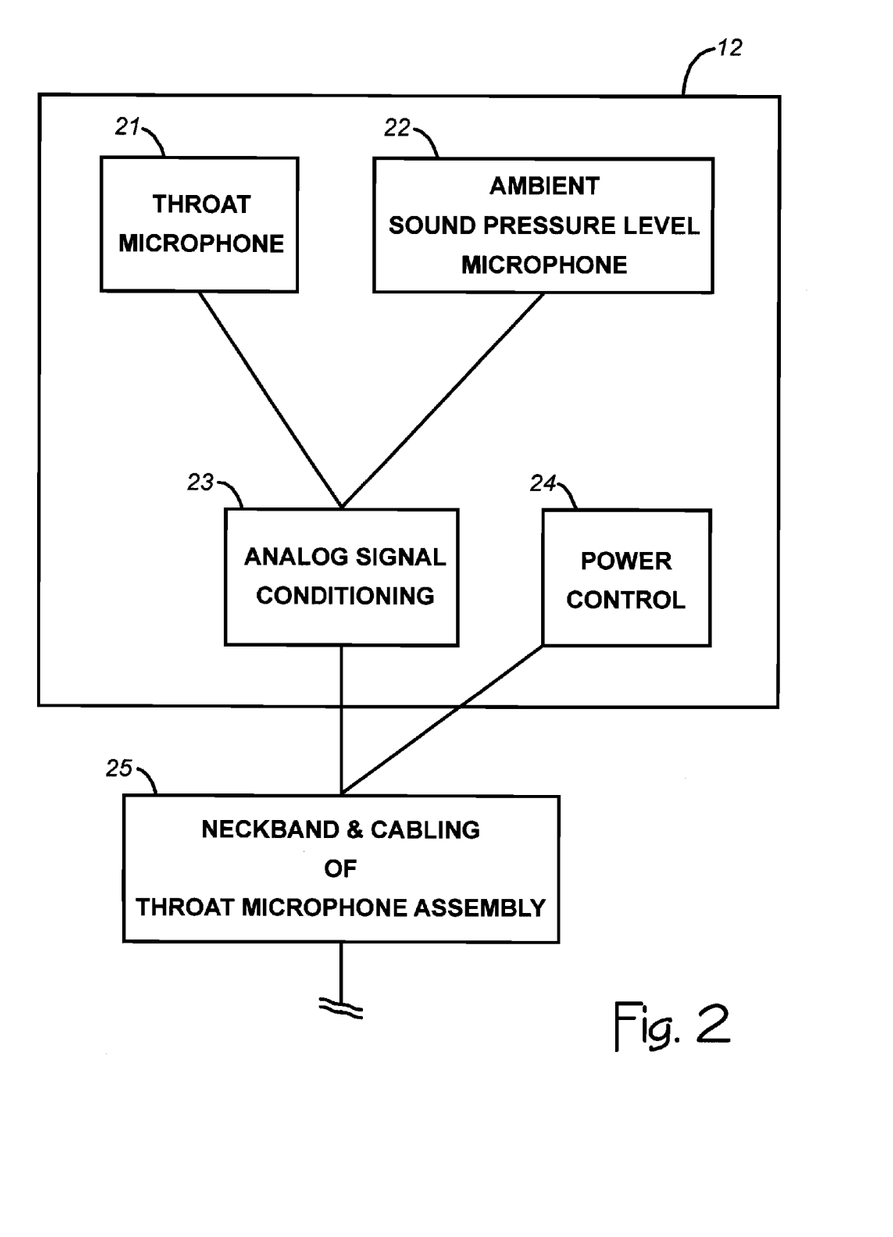
FIG. 2 is a block diagram of a sensor subassembly portion of the throat microphone assembly (i.e., a vocal activity input portion)

Preferably, the sensor subassembly 12 includes multiple sensor elements as shown in the block diagram of FIG. 2. A first sensor element 21, that is labeled in FIG. 2 as a "throat microphone," functions as means for sensing vibrations of the neck of the user that result from speech produced by the user. It may take the form of a known type of contact microphone (e.g., with an accelerometer element). A second sensor element 22 (e.g., a piezoelectric or other open-air microphone element), that is labeled in FIG. 2 as an "ambient sound pressure microphone," functions as acoustic-to-electric transducer means for sensing ambient sounds other than vibrations of the neck.

With the neckband 11 of the throat microphone assembly 10 in a normal operating position on the user's neck, the first sensor element 21 is directed posteriorly toward the user's neck to sense neck vibrations, while the second sensor element 22 is directed laterally (i.e., sideways) to sense ambient sounds. The first and second sensor elements 21 and 22 are coupled to an "analog signal condition" circuit 23 that is, in turn, coupled, along with a "power control" circuit 24, by cabling to the neckband 11 (i.e., the "neckband & cabling of the throat microphone assembly" depicted by a block 25 in FIG. 2). That cabling includes separate electric lines (e.g., wires strung within the neck band 11) such that each electric line couples the output (i.e., an electrical signal) of a respective one of the first and second sensor elements 21 and 22 to the module subassembly 13.

Figure 3:
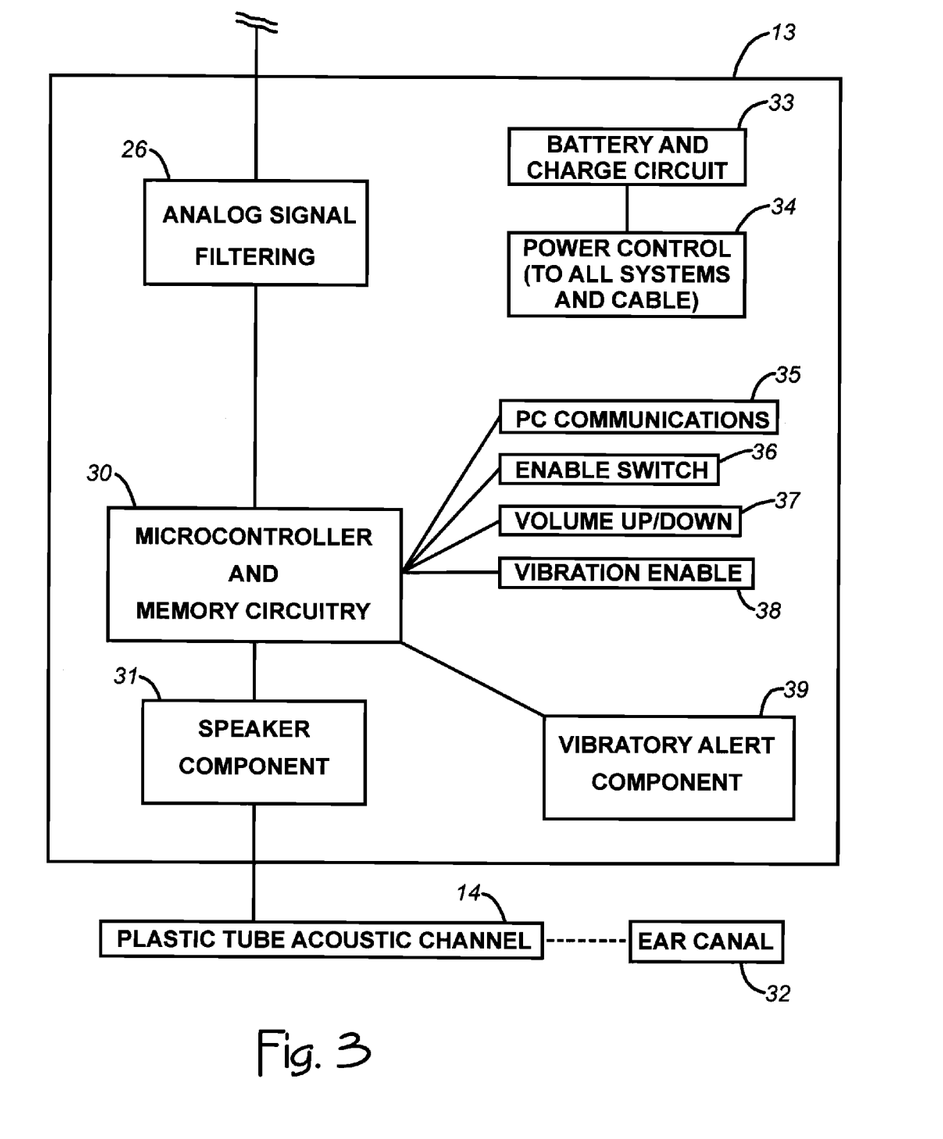
FIG. 3 is a block diagram of a module subassembly portion of the throat microphone assembly (i.e., an electronic module and output portion)

The block diagram of FIG. 3 illustrates various components of the module subassembly 13 portion of the throat microphone assembly 10. The electrical signal from the block 25 in FIG. 2 is filtered by an analog signal filtering circuit (depicted by a block 26) to produce a filtered electrical signal that is coupled to microcontroller and memory circuitry depicted by a block 30. The microcontroller and memory circuitry (e.g., a known type of digital computer circuitry operating under program control) processes that filtered electrical signal to determine the characteristics of the speech produce by the user; it then determines whether or not those characteristics fall within specified parameters for acceptable and/or unacceptable voicing. Based upon that determination, the microcontroller and memory circuitry produces a loudness alert waveform (using a then current loudness alert type). That loudness alert waveform is coupled to a speaker component 31 to produce an audible loudness alert that is coupled by the plastic tube acoustic channel 14 to the ear canal 32 of the user.

Preferably, the module subassembly 13 includes a battery and charging circuit (block 33 in FIG. 3) with a power control (block 34) that distributes power as required to all components of the system. A universal serial bus (USB) or other personal computer (PC) communications port (block 35) enables communication between a PC or other computer (not shown) and the microcontroller and memory circuitry for programming and other purposes. User controls include an ENABLE switch (block 36) for turning the system ON and OFF, volume UP and DOWN buttons (block 37) for varying the volume of loudness alerts, and a vibration-enabling control (block 38) for enabling use of a vibratory alert component (block 39) in cases where the user desires an inaudible vibratory loudness alert instead of an audible loudness alert.

Based upon the foregoing description, a person having ordinary skill in the art can readily implement the subassemblies described above using known types of components and circuit design and programming techniques. The circuitry of the module subassembly 13, for example, may include any of various known digital microcontrollers and memory components that operate under program control. They are configured to perform as described in the sense that they are interconnected and programmed to function as stated.

Figure 4:
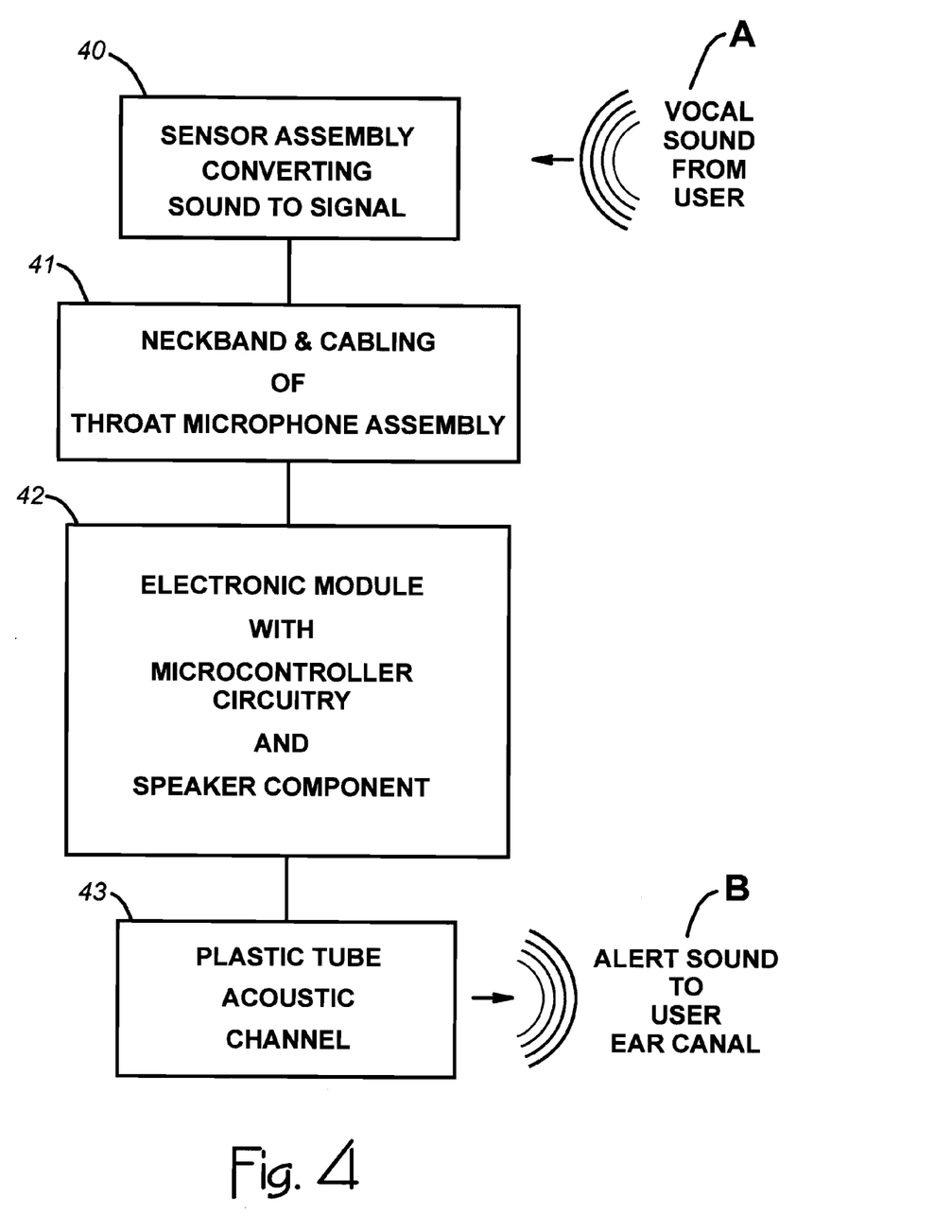
FIG. 4 of the drawings is an overall block diagram of the throat microphone assembly performing its function of receiving vocal sounds from the user and producing loudness alerts to the user.

FIG. 4 summarizes use of the assembly 10, showing the assembly 10 receiving vocal sounds produce by the user, as depicted at a reference letter A in FIG. 2, and producing loudness alerts to the user's ear canal as depicted at a reference letter B. The sensor assembly described previously converts sound to an electrical signal (as depicted by a block 40 in FIG. 4), the neckband and cabling of the throat microphone assembly couples that electrical signal to the module subassembly (as depicted by block 41), the module subassembly processes the electrical signal and produces an audible loudness alert (block 42), and the plastic-tube acoustic channel (block 43) couples the audible loudness alert to the user.

Figure 5:
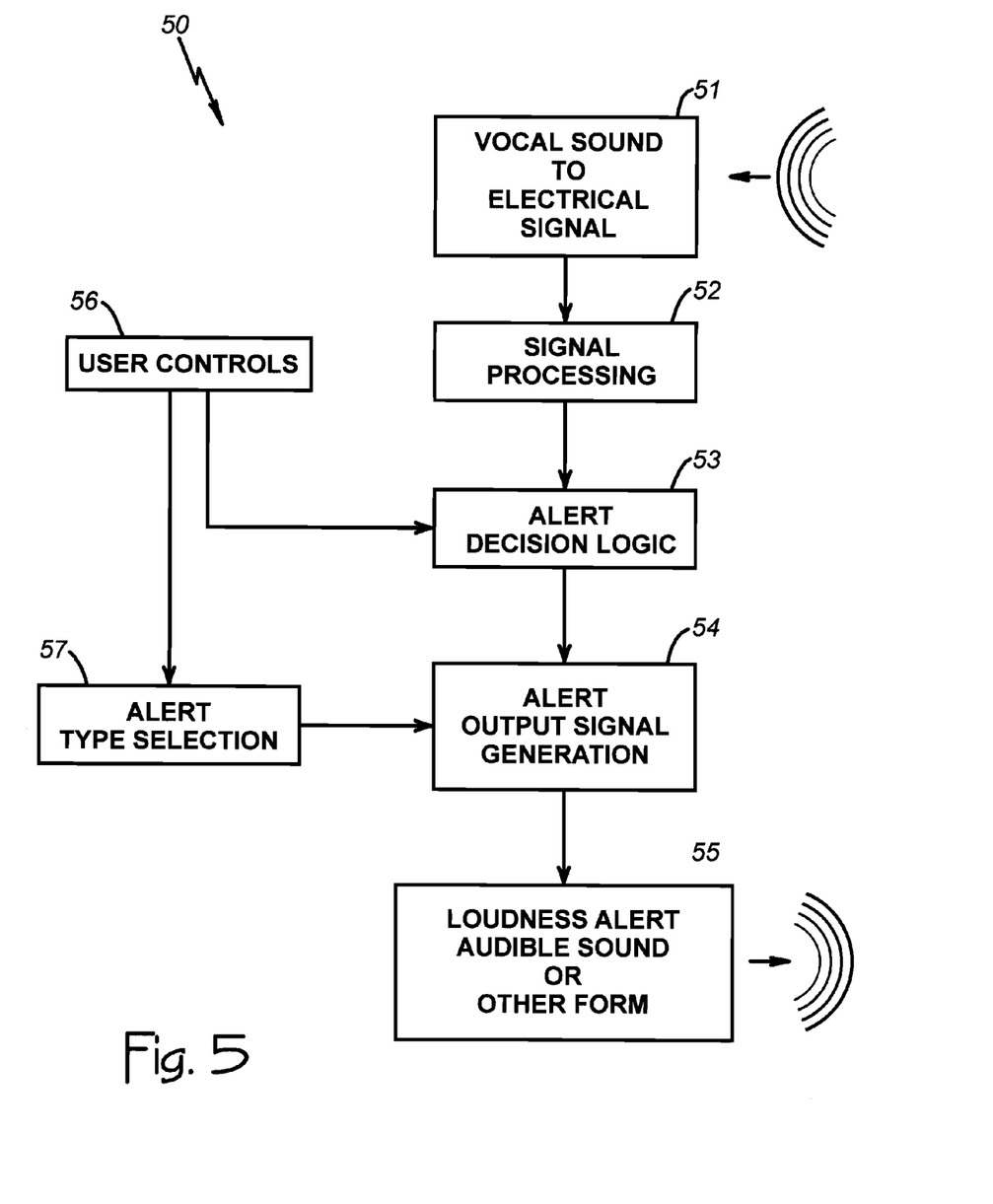
FIG. 5 is a block diagram of a first embodiment of a voice-monitoring system constructed according to the present invention that provides multiple loudness alert types.
Figure 6:
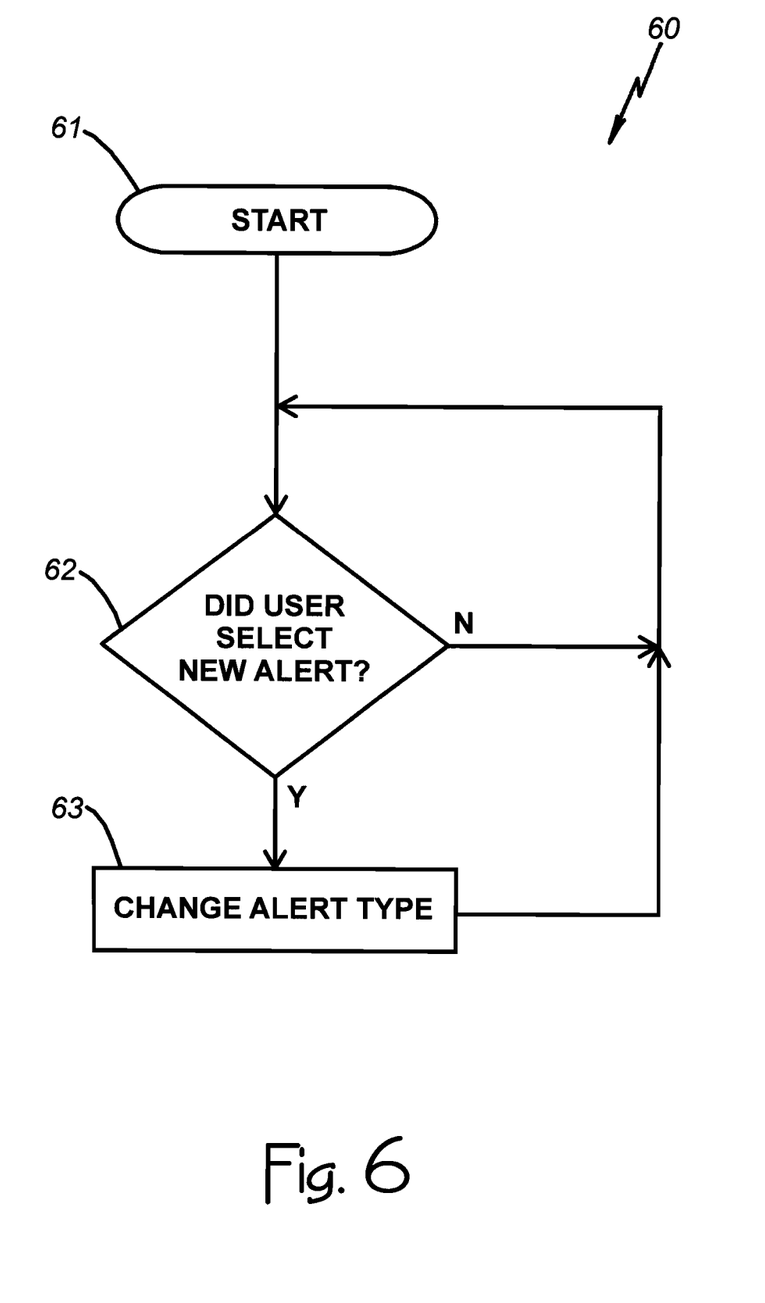
FIG. 6 is a flow chart showing logical steps performed by the first embodiment.
Figure 7:
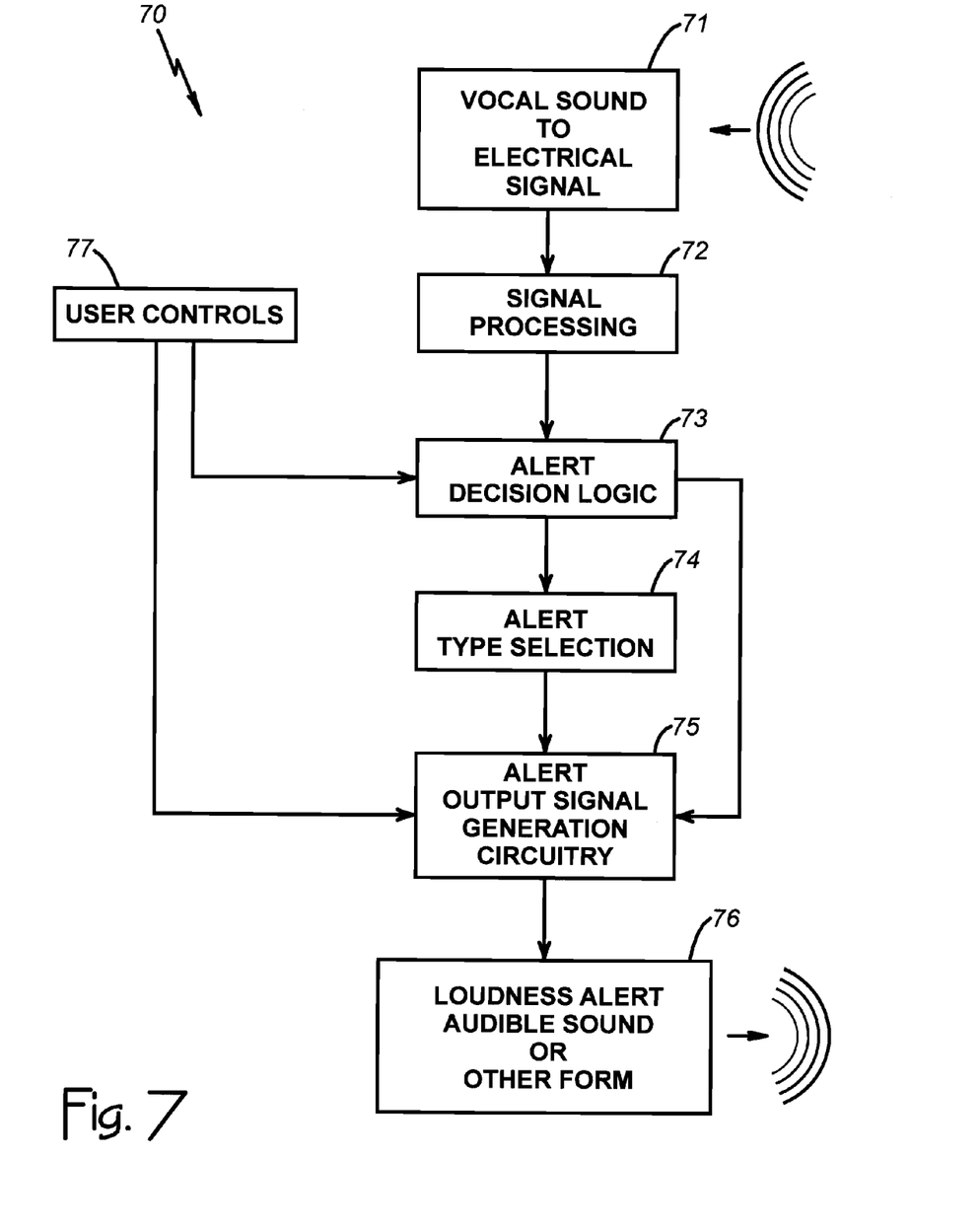
FIG. 7 is a block diagram showing functional aspects of a second embodiment of a voice-monitoring system constructed according to a first aspect of the present invention.
Figure 8:
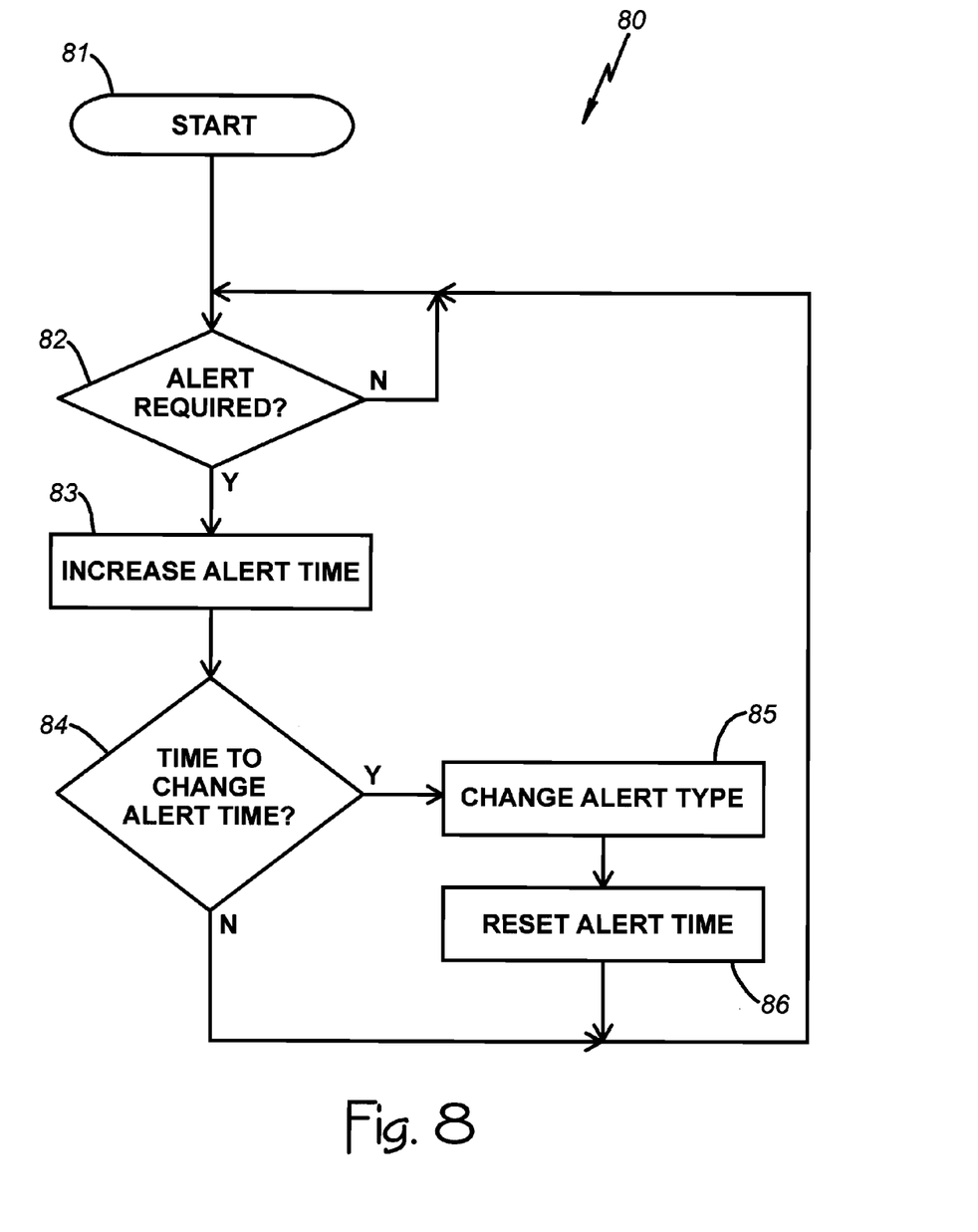
FIG. 8 is a flow chart showing logical steps performed by the second embodiment.

Turn now to FIGS. 5-11 with the foregoing information in mind. FIGS. 5 and 6 concern changing the current loudness alert type based upon a selection made by the user with the user controls. FIGS. 7 and 8 concern changing loudness alert type based upon accumulated usage of the current loudness alert type, and FIGS. 9 and 10 concern changing loudness alert type based upon effectiveness of the current loudness alert type. In each case, multiple loudness alert types (e.g., five different types) are stored in the microcontroller, and each one may take the form of any of various types of known types of audio files for various tones, beeps, wave files, speech, and so forth that is suitable to be used to alert the user that their voicing is outside acceptable limits.

First consider a block diagram 50 in FIG. 5. The user's vocal activity is measured, including filtering the electrical signal and determining its characteristics, as indicated by blocks 51 and 52. The alert decision logic at a block 53 determines if the characteristics of the electrical signal fall within parameters for unacceptable voicing. Loudness alert output signal generation (i.e., generation of a loudness alert waveform) occurs at a block 54 based upon the current loudness alert type. That waveform is then converted to an audible sound or other form of loudness alert (e.g., a vibratory loudness alert). The user sets parameters for unacceptable voicing and loudness alert volume by user-operation of user controls indicated by a block 56. Loudness alert type selection occurs at a block 57, and the user also has the ability to change the current loudness alert type via the user controls.

A flow chart 60 in FIG. 6 shows the logic involved in a subroutine for changing loudness alert type. The subroutine begins at a block 61 and proceeds to a decision block 62 where it periodically checks if the user selected a different loudness alert type than the currently used loudness alert type. If the user did not ("N"), the subroutine returns to the input of the decision block 62. If the user did select a different loudness alert type than the currently used loudness alert type ("Y"), the subroutine changes the current loudness alert type at a block 63 to that selected by the user and then returns to the input of the decision block 62.

Restating the foregoing using claim language presented later on, the speech therapy system 10 is a portable voice-monitoring assembly for a user to carry and use as an aid to maintaining their speech in a specified range of acceptable voicing. The portable voice-monitoring assembly includes a voice-sensing first subassembly portion 12 that functions as voice-sensing means for producing an electrical signal indicative of speech spoken by the user. It also includes an alert-producing second subassembly portion 13 that functions as electronic circuit means for receiving the electrical signal and producing a loudness alert to the user when the electrical signal indicates that the speech spoken by the user falls outside the specified range of acceptable voicing. According to a first aspect illustrated by FIGS. 5 and 6, the alert-producing second subassembly 13 is configured to produce a plurality of loudness alert types, and to produce a loudness alert therefrom using a selected one of those loudness alert types. It is so configured in the sense that it includes components interconnected and programmed to function as described.

Now consider a block diagram 70 in FIG. 7. It illustrates the overall process of changing loudness alert types based upon accumulated usage. The user's vocal activity is measured, including filtering the electrical signal and determining its characteristics, as indicated by blocks 71 and 72. The loudness alert decision logic at a block 73 determines if the characteristics of the electrical signal fall within parameters for unacceptable voicing. The loudness alert type is then selected at a block 74 and loudness alert output signal generation (i.e., generation of an alert waveform) occurs at a block 75 based upon the current alert type. That waveform is then converted to an audible sound or other form of alert as indicated by a block 76. The user sets parameters for unacceptable voicing and loudness alert volume using user controls indicated by a block 77.

A flow chart 80 in FIG. 8 shows the logic involved in a subroutine for changing loudness alert type based upon accumulated usage. The subroutine begins at a block 81 and proceeds to a decision block 82 where it periodically checks if a loudness alert is currently required (based upon voicing characteristics). If a loudness alert is not currently required ("N"), the subroutine returns to the input of the decision block 82. If a loudness alert is currently required ("Y"), the subroutine incrementally increases a USAGE TIME parameter in memory at a block 83 (a parameter that indicates how long the current loudness alert type has been used).

Regarding the "USAGE TIME" name used herein (including the claims), it is an arbitrary label assigned to the parameter in memory (i.e., the parameter that indicates accumulated usage as described above). It serves as a simple mnemonic. Other names may be used within the scope of the claims as a label for the parameter instead.

From the block 83, the subroutine proceeds to a decision block 84 to determine if the time has come to change the loudness alert type based upon the value of the USAGE TIME parameter. If the value of the USAGE TIME parameter exceeds a specified value (e.g., a specified value within a three-second to four-second range), that fact is taking as indicating the time has come to change the loudness alert type ("Y") and the subroutine proceeds to change the current loudness alert type at a block 85 in addition to resetting the USAGE TIME parameter to an initial value at a block 86. The subroutine then returns to the input of the decision block 82. If the value of the USAGE TIME parameter does not exceed the specified value, that fact is taking as indicating that the time has not yet come to change the loudness alert type ("N"), in which case the subroutine proceeds directly to the input of the decision block 82 without changing the current loudness alert type. Restating this usage-time aspect of the present invention using claim language presented later on, the alert-producing second subassembly 13 is configured to record a USAGE TIME parameter for a currently used loudness alert type, and to change the currently used loudness alert type when the USAGE TIME parameter exceeds a specified value.

Figure 9:
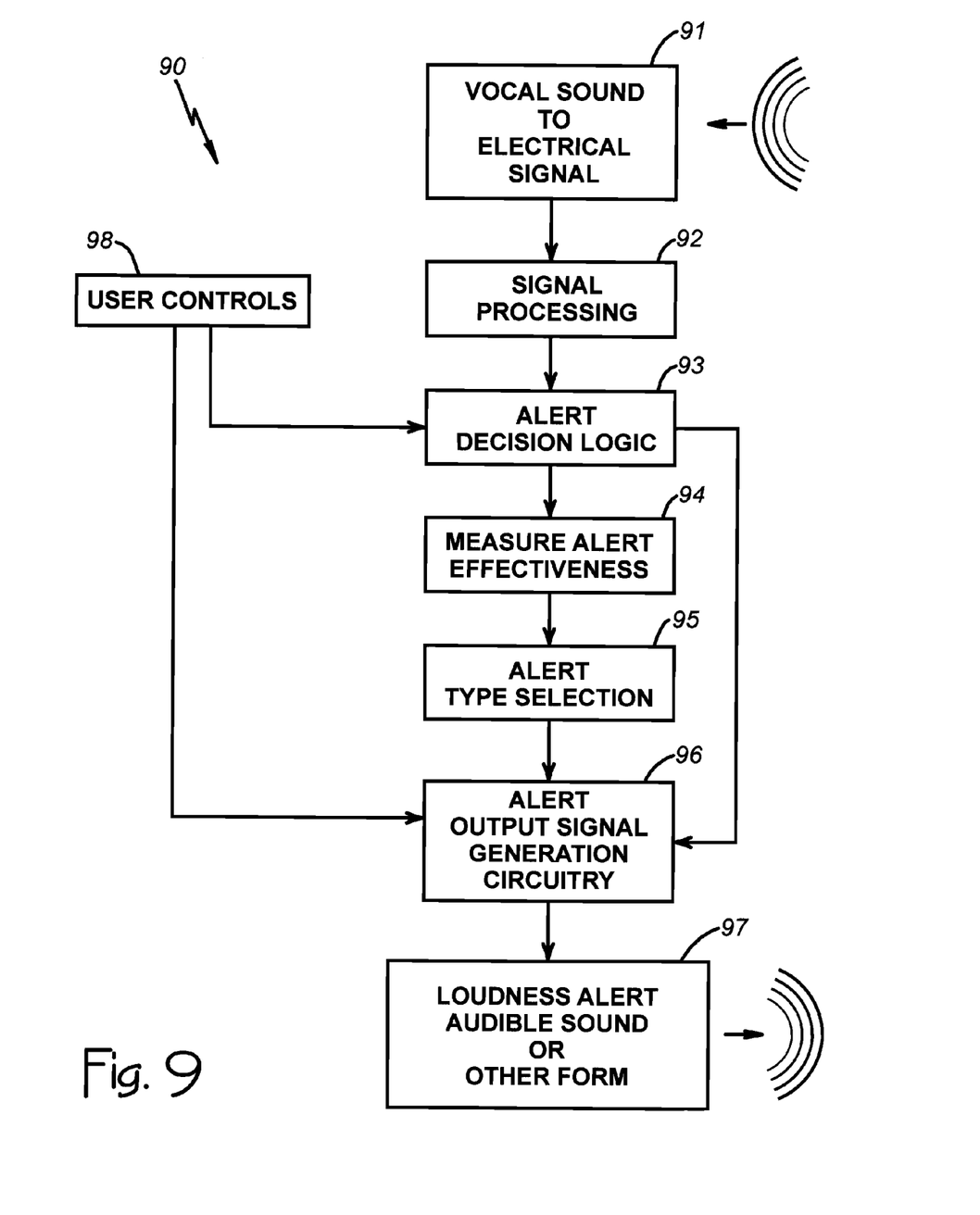
FIG. 9 is a block diagram showing functional aspects of a third embodiment of a voice-monitoring system constructed according to the present invention that includes effectiveness-based selection of loudness alerts.

Next, consider a block diagram 90 in FIG. 9. It illustrates the overall process of changing loudness alert types based upon effectiveness. The user's vocal activity is measured, including filtering the electrical signal and determining its characteristics, as indicated by blocks 91 and 92. The loudness alert decision logic at a block 93 determines if the characteristics of the electrical signal fall within parameters for unacceptable voicing. A block 94 measures the effectiveness of the current loudness alert type, and a block 95 determines the loudness alert type to be generated. Loudness alert output signal generation (i.e., generation of an alert waveform) occurs at a block 96 based upon the current alert type. That waveform is then converted to an audible sound or other form of alert as indicated by a block 97. The user sets parameters for unacceptable voicing and loudness alert volume using user controls indicated by a block 98.

Figure 10:
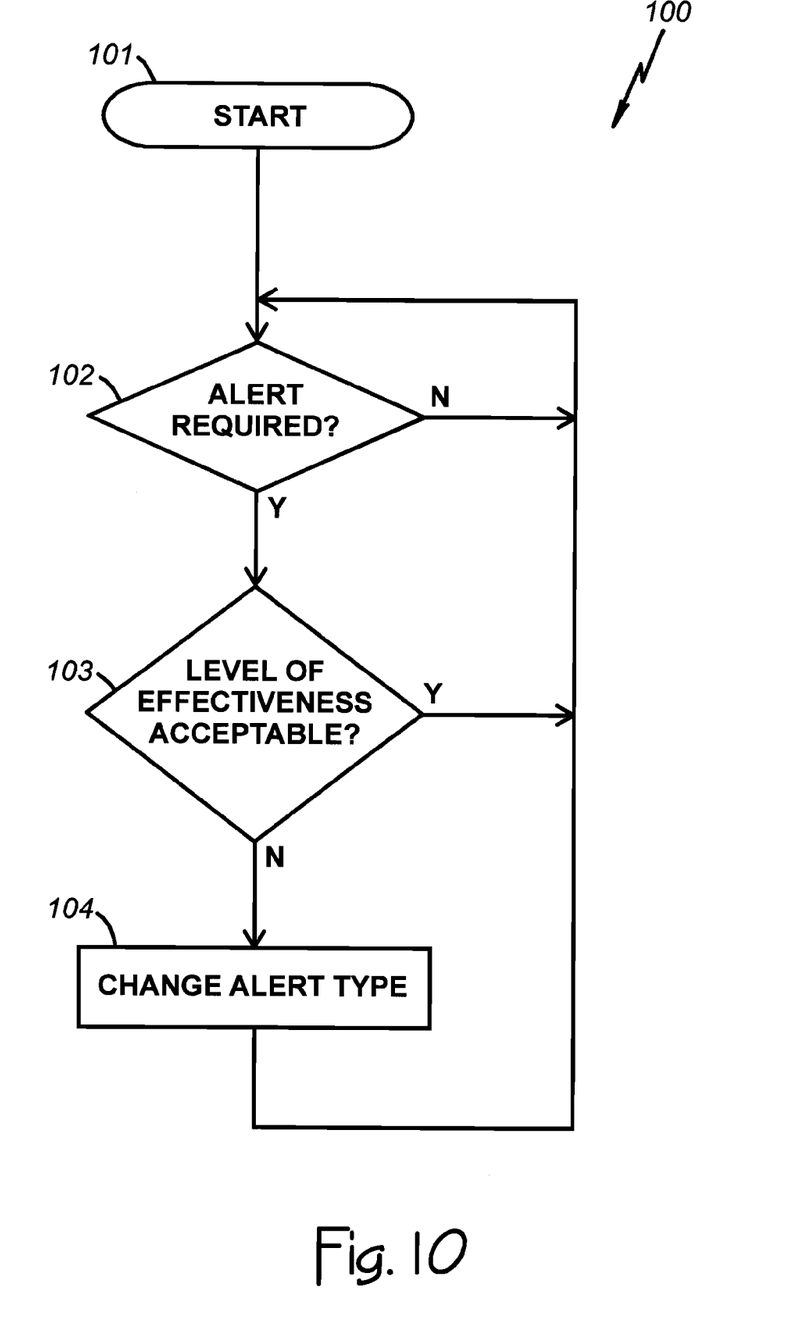
FIG. 10 is a flow chart showing logical steps performed by the third embodiment.

A flow chart 100 in FIG. 10 shows the logic involved in a subroutine for changing loudness alert type based upon effectiveness. The subroutine begins at a block 101 and proceeds to a decision block 102 where it periodically checks if a loudness alert is currently required (based upon voicing characteristics). If a loudness alert is not currently required ("N"), the subroutine returns to the input of the decision block 102. If a loudness alert is currently required ("Y"), the subroutine proceeds to a decision block 103 where it checks if the level of effectiveness of the current loudness alert type is acceptable. In other words, if the alert decision block 102 determines that a loudness alert is required, the effectiveness decision block 103 decides whether the loudness alert type should be changed. If the effectiveness is above a specified level ("Y"), the subroutine returns to the input of the decision block 102. If the effectiveness is not above the specified level ("N"), the subroutine changes the loudness alert type to the next loudness alert type available and returns to the input of the decision block 102.

In terms of some related claim language, the alert-producing second assembly 13 is configured to record an EFFECTIVENESS parameter for the currently used loudness alert type. That EFFECTIVENESS parameter is based upon the duration of use of the currently used loudness alert type before the user adjusts their speech to within the specified range of acceptable voicing. It indicates how long the current loudness alert type is used before the user transitions to acceptable voicing, and the alert-producing second subassembly is configured to change the currently used loudness alert type if the EFFECTIVENESS parameter falls below a specified level. A catalog of loudness alert types is maintained in memory along with an EFFECTIVENESS parameter for each one, and the block 104 changes loudness alert type by favoring loudness alert types having greater effectiveness. Of course, the "EFFECTIVENESS" name herein and in the claims is also an arbitrary label given to the parameter in memory that indicates effectiveness as described above. It serves as a simple mnemonic. Other names labels may be used as a label for the parameter instead, within the scope of the claims.

Figure 11:
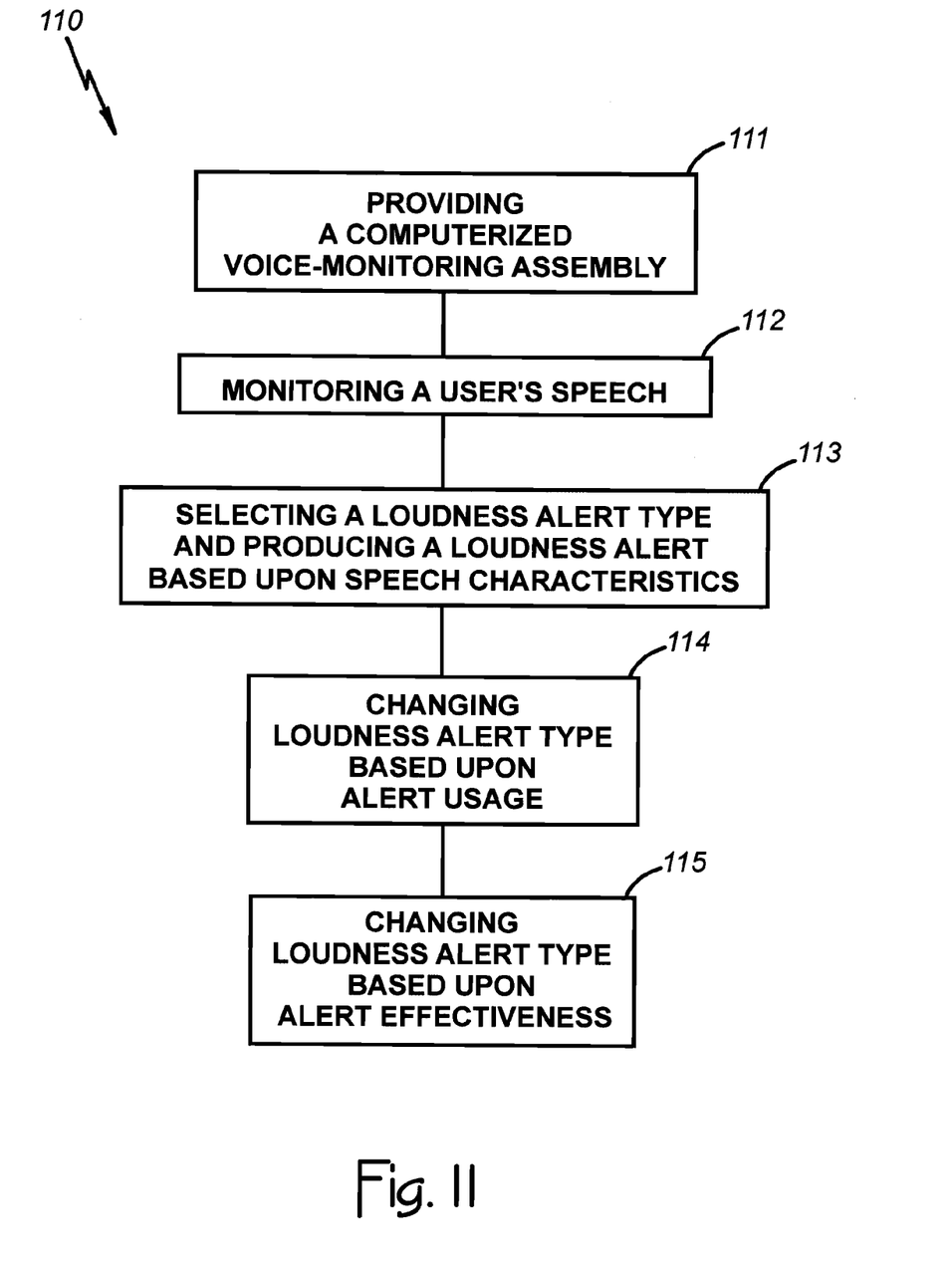
FIG. 11 is a block diagram of the methodology of the present invention.

A block diagram 110 in FIG. 11 summarizes the methodology of the present invention. The method includes the step of providing a portable voice-monitoring assembly as described above for the user to carry as a speech therapy system (block 111). The method proceeds by monitoring the speech of the user with the voice-monitoring assembly (block 112), determining with the voice-monitoring assembly if the speech falls outside the specified range of acceptable voicing (block 113), selecting with the second subassembly one of the plurality of loudness alert types to be used as the currently used loudness alert type (block 114), and producing a loudness alert with the second subassembly using the currently used loudness alert type if the speech falls outside the specified range of acceptable voicing (block 115). Preferably, the currently used loudness alert is selected based upon a USAGE TIME parameter and/or an EFFECTIVENESS parameter.

Figure 12:
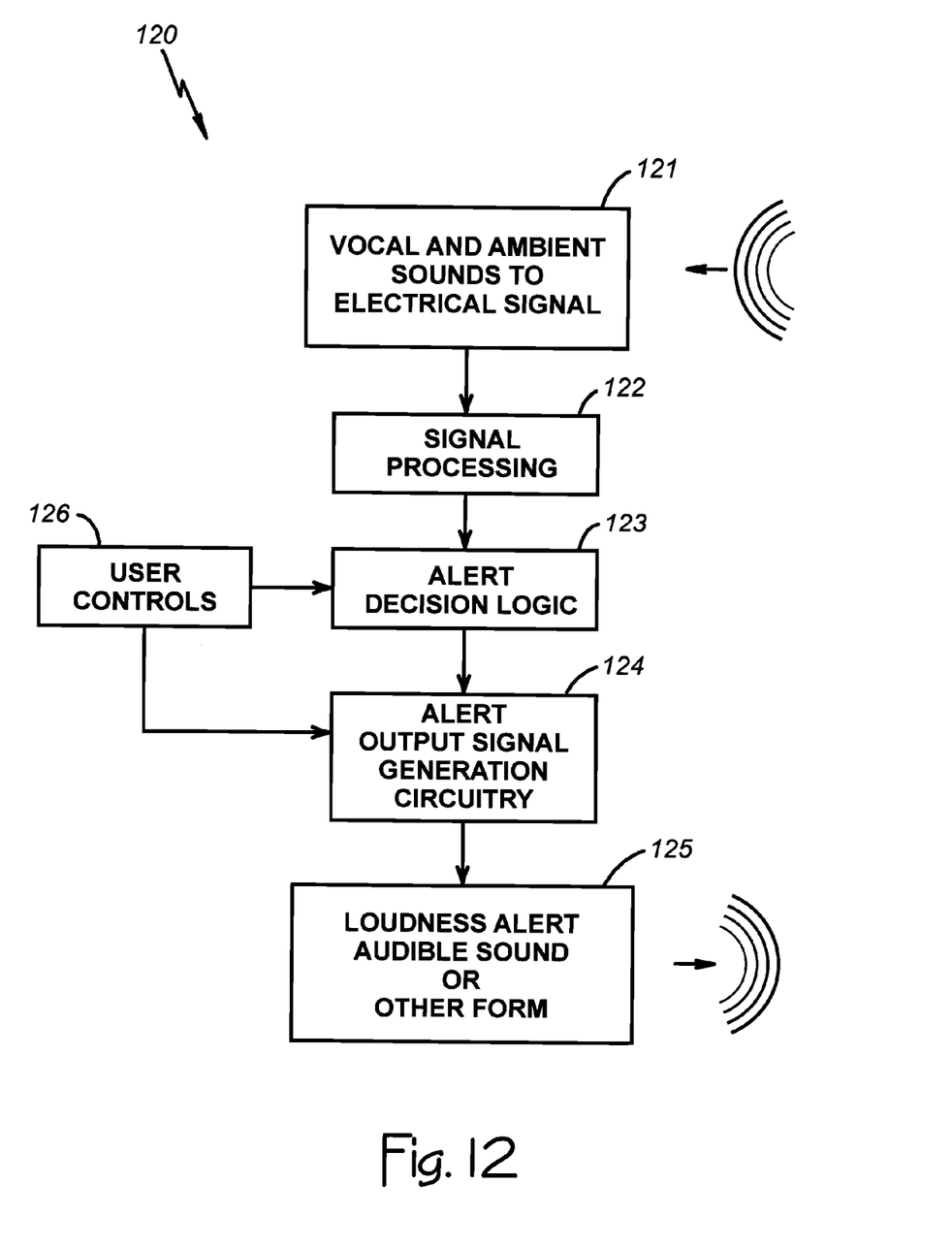
FIG. 12 is a block diagram showing functional aspects of a two-level fourth embodiment of a voice-monitoring system constructed according to the present invention.
Figure 13:
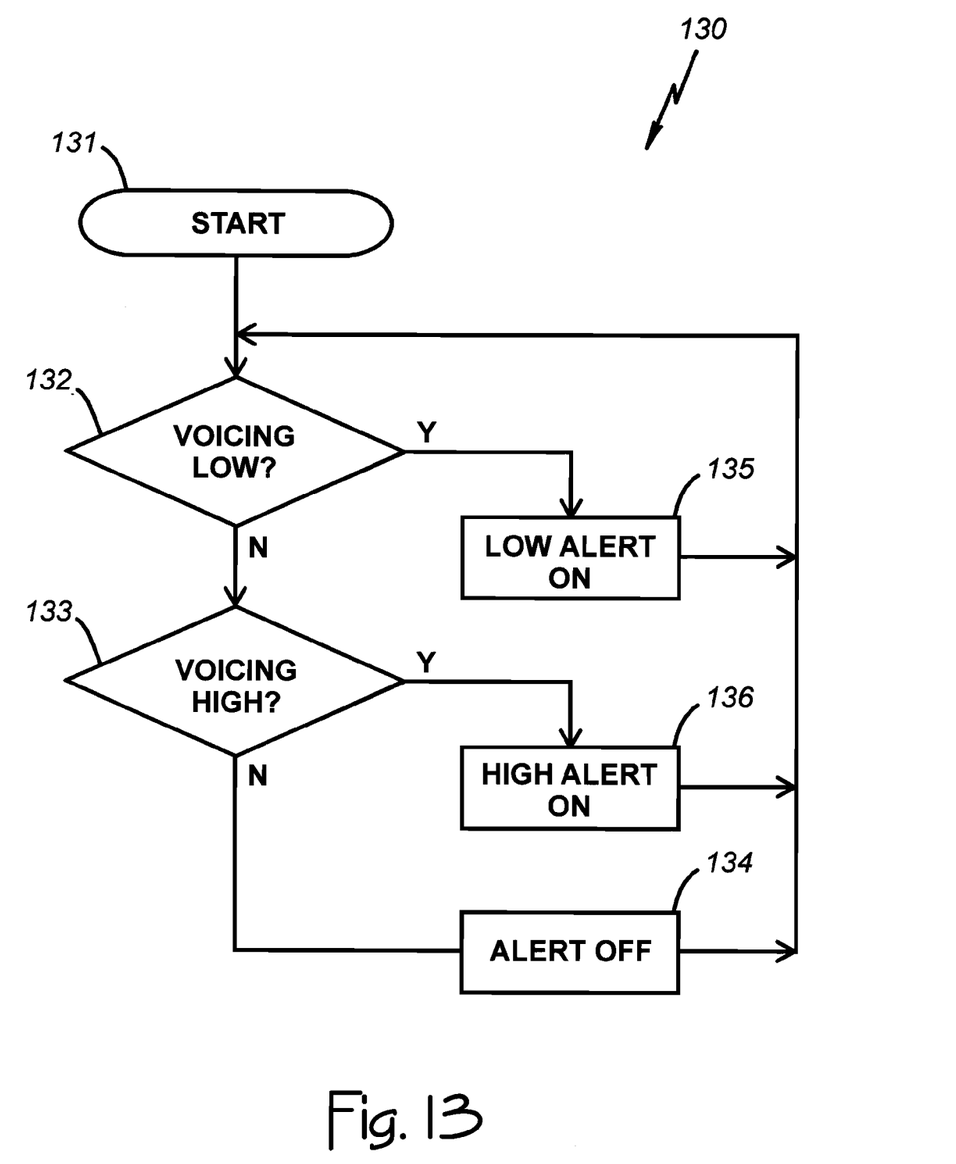
FIG. 13 is a flow chart showing logical steps performed by the fourth embodiment.

The specified range of acceptable voicing mentioned above may be a speech level below a TOO HIGH level (a parameter in memory) that has been set by the user with the user controls; if the speech level rises above the TOO HIGH level, a TOO HIGH loudness alert is produce that indicates that the speech level is too high (i.e., too loud). Alternatively, the specified range of acceptable voicing may be a speech level above a TOO LOW level (a parameter in memory) that has been set by the user; if the speech level falls below the TOO LOW level, a TOO LOW loudness alert is produce that indicates that the speech level is too low (i.e., too soft). In either case, the second subassembly is configured to consider ambient noise sensed by the second sensor element 22 of the sensor subassembly 12 by varying the level of the operative one of the TOO HIGH level and the TOO LOW level according to the level of ambient noise; as the ambient noise increases, the subassembly increases the operative one of the TOO HIGH level and the TOO LOW level; as the ambient noise decreases, the subassembly decreases the operative one of the TOO HIGH level and the TOO LOW level FIGS. 12 and 13 illustrate various aspects of a two-level fourth embodiment of the invention for which the second subassembly is configured to compare the speech level with both a TOO HIGH level and a TOO LOW level. As indicated by a block diagram 120 in FIG. 12, the user's vocal activity is measured, including filtering the electrical signal and determining its characteristics, as indicated by blocks 121 and 122. The loudness alert decision logic at a block 123 determines if the characteristics of the electrical signal fall within parameters for unacceptable voicing. Loudness alert output signal generation (i.e., generation of an alert waveform) occurs at a block 124 based upon the current alert type. That waveform is then converted to an audible sound or other form of alert as indicated by a block 125. The user sets parameters for unacceptable voicing and loudness alert volume, including the TOO HIGH level and the TOO LOW level, using user controls indicated by a block 126. The block 124 produces a TOO-HIGH-INDICATING loudness alert if the speech falls above the TOO-HIGH parameter; it produces a TOO-LOW-INDICATING loudness alert if the speech falls below a TOO-LOW parameter.

A flow chart 130 in FIG. 13 shows the logic involved in a subroutine for changing loudness alert type based the TOO HIGH level and the TOO LOW level technique. The subroutine begins at a block 131 and proceeds to a decision block 132 where it checks if the voicing is below the minimum acceptable threshold level (i.e., it is too low). If the voicing is not too low ("N"), the subroutine proceeds to a decision block 133 where it checks if the voicing is above the maximum acceptable threshold level (i.e., it is too high). If the voicing is not too high ("N"), the alerts are disabled (i.e., the voicing is neither too low or too high) and the subroutine returns to the block 132. If, however, the decision block 132 determines that the voicing is too low ("Y"), a block 135 turns on the appropriate alert to signal to the user that the voicing is too low. Similarly, if the decision block 133 determines that the voicing is too high ("Y"), a block 136 turns on the appropriate alert to signal to the user that the voicing is too high.

Thus, the invention provides a speech therapy system and method with loudness alerts that significantly aid a user in maintaining their speech within a range of acceptable voicing. Based upon the foregoing description taken in conjunction with the drawings and the claims, a person having ordinary skill in the art can readily implement the structural aspects and practice the methodology of the present invention. Although exemplary embodiments have been shown and described, one of ordinary skill in the art may make many changes, modifications, and substitutions without necessarily departing from the spirit and scope of the invention. As for the specific terminology used to describe the exemplary embodiments, it is not intended to limit the invention. Each specific term is intended to include all technical equivalents that operate in a similar manner to accomplish a similar purpose or function.

What is claimed is:

1. A speech therapy system, comprising:
 a portable voice-monitoring assembly for a user to carry and use as an aid to maintaining their speech in a specified range of acceptable voicing;
 a voice-sensing first subassembly portion of the portable voice-monitoring assembly that functions as voice-sensing means for producing an electrical signal indicative of speech spoken by the user; and
 an alert-producing second subassembly portion of the portable assembly that functions as electronic circuit means for receiving the electrical signal and producing a loudness alert to the user when the electrical signal indicates that the speech spoken by the user falls outside the specified range of acceptable voicing;
 wherein the alert-producing second subassembly is configured to produce a plurality of loudness alert types and to produce a loudness alert using a selected one of said plurality of loudness alert types;
 the alert-producing second subassembly is configured to record a USAGE TIME parameter for a currently used loudness alert type; and
 the alert-producing second subassembly is configured to change the currently used loudness alert type when the USAGE TIME parameter exceeds a specified value.

2. A speech therapy system, comprising:
 a portable voice-monitoring assembly for a user to carry and use as an aid to maintaining their speech in a specified range of acceptable voicing;
 a voice-sensing first subassembly portion of the portable voice-monitoring assembly that functions as voice-sensing means for producing an electrical signal indicative of speech spoken by the user; and
 an alert-producing second subassembly portion of the portable assembly that functions as electronic circuit means for receiving the electrical signal and producing a loudness alert to the user when the electrical signal indicates that the speech spoken by the user falls outside the specified range of acceptable voicing;
 wherein the alert-producing second subassembly is configured to produce a plurality of loudness alert types and to produce a loudness alert using a selected one of said plurality of loudness alert types;
 wherein the alert-producing second assembly is configured to record an EFFECTIVENESS parameter for a currently used loudness alert type;
 wherein the EFFECTIVENESS parameter for the currently used loudness alert type is based upon the duration of use of the currently used loudness alert type before the user adjusts their speech to within the specified range of acceptable voicing; and
 wherein the alert-producing second subassembly is configured to change the currently used loudness alert type if the EFFECTIVENESS parameter falls below a specified level.

3. A method for producing a loudness alert when the speech of the user falls outside a specified range of acceptable voicing, the method comprising:
 providing a portable voice-monitoring assembly for the user to carry as a speech therapy system, said assembly including (i) a voice-sensing first subassembly that produces an electrical signal indicative of speech spoken by the user, and (ii) an alert-producing second subassembly that is configured to process the electrical signal and produce a selected one of a plurality of loudness alert types as feedback to the user;
 monitoring the speech of the user with said voice-monitoring assembly;
 determining with said voice-monitoring assembly if the speech falls outside the specified range of acceptable voicing;
 selecting with the second subassembly one of the plurality of loudness alert types to be used as the currently used loudness alert type;
 producing a loudness alert with the second subassembly using the currently used loudness alert type if the speech falls outside the specified range of acceptable voicing;
 using a specific loudness alert type as a currently used loudness alert type that is to be used to produce loudness alerts;
 producing a loudness alert with the second subassembly using the currently used loudness alert type;
 recording with the second subassembly a USAGE TIME parameter for the currently used loudness alert type;
 using a different loudness alert type as the currently used loudness alert type, in conjunction with resetting the USAGE TIME parameter, if the USAGE TIME parameter exceeds a specified value; and producing the loudness alert using the currently used loudness alert type as so changed and currently existing.

4. A method as recited in claim 3, further comprising:

producing a TOO-HIGH-INDICATING loudness alert with the second subassembly if the speech falls above a TOO-HIGH parameter; and producing a TOO-LOW-INDICATING loudness alert with the second subassembly if the speech falls below a TOO-LOW parameter.

5. A method for producing a loudness alert when the speech of the user falls outside a specified range of acceptable voicing, the method comprising:

providing a portable voice-monitoring assembly for the user to carry as a speech therapy system, said assembly including (i) a voice-sensing first subassembly that produces an electrical signal indicative of speech spoken by the user, and (ii) an alert-producing second subassembly that is configured to process the electrical signal and produce a selected one of a plurality of loudness alert types as feedback to the user;

monitoring the speech of the user with said voice-monitoring assembly;

determining with said voice-monitoring assembly if the speech falls outside the specified range of acceptable voicing;

selecting with the second subassembly one of the plurality of loudness alert types to be used as the currently used loudness alert type;

producing a loudness alert with the second subassembly using the currently used loudness alert type if the speech falls outside the specified range of acceptable voicing;

recording with the second subassembly an EFFECTIVENESS parameter for a currently used loudness alert type based upon the duration of use of the currently used loudness alert type before the user adjusts their speech to within the specified range of acceptable voicing;

changing the currently used loudness alert type, in conjunction with resetting the EFFECTIVENESS parameter, if the EFFECTIVENESS parameter falls below a specified level; and producing the loudness alert using the currently used loudness alert type as so changed and currently existing.

6. A method as recited in claim 5, further comprising:

producing a TOO-HIGH-INDICATING loudness alert with the second subassembly if the speech falls above a TOO-HIGH parameter; and producing a TOO-LOW-INDICATING loudness alert with the second subassembly if the speech falls below a TOO-LOW parameter.

\* \* \* \* \*